United States Patent [19]

Neil, Jr. et al.

[11] Patent Number: 4,894,486

[45] Date of Patent: Jan. 16, 1990

[54] STABILIZER FOR BISPHENOLS AND PROCESS OF USING SAME

[75] Inventors: Lawrence E. Neil, Jr., Angleton; Theodore J. Gormanos, Lake Jackson, both of Tex.

[73] Assignee: The Dow Chemical Company, Midland, Mich.

[21] Appl. No.: 289,083

[22] Filed: Dec. 22, 1988

[51] Int. Cl.$^4$ .............................................. C07C 37/88
[52] U.S. Cl. .................................. 568/702; 568/701; 568/703; 568/724
[58] Field of Search ................ 568/701, 702, 724, 703

[56] References Cited

U.S. PATENT DOCUMENTS

| | | | |
|---|---|---|---|
| 2,965,539 | 12/1960 | Loper et al. | 568/702 |
| 3,629,339 | 12/1971 | Schlichting et al. | 568/724 |
| 3,855,150 | 12/1974 | Weris, III | 568/724 |
| 4,054,611 | 10/1977 | Mimaki et al. | 568/781 |
| 4,160,110 | 7/1979 | Carnahan, Jr. | 568/703 |
| 4,289,587 | 9/1981 | Christena | 568/702 |
| 4,359,590 | 11/1982 | Dachs et al. | 568/702 |

FOREIGN PATENT DOCUMENTS

| | | | |
|---|---|---|---|
| 320474 | 1/1972 | U.S.S.R. | 568/701 |
| 0890432 | 2/1962 | United Kingdom | 568/724 |
| 1022583 | 3/1966 | United Kingdom | 568/724 |

OTHER PUBLICATIONS

Goerlitz, "Chemical Abstracts", vol. 87(1977), 119413.
Patzschke et al, "Chemical Abstracts", vol. 92(1979), 7930m.
Patricca et al., "Chemical Abstracts", vol. 96(1982), 124631h.

*Primary Examiner*—Werren B. Lone

[57] ABSTRACT

Lactic, malic and glyceric acids have been found to be superior to the hydroxy acids here-to-fore employed for the stabilization of bisphenols. These hydroxy carboxylic acids or their ammonium or alkali metal salts can be added to the feed reactants used to make the bisphenols or to the reaction mixture after the reaction is complete or at any point in between. They are particularly useful when the bisphenol is exposed to high temperatures, e.g. during the separation of the bisphenol from the reaction mixture or in a melt.

11 Claims, No Drawings

STABILIZER FOR BISPHENOLS AND PROCESS OF USING SAME

BACKGROUND OF THE INVENTION

Most polymers are generally thought to be heat and oxygen sensitive and tend to degrade to form products which have an adverse effect on their color as well as their physical properties. Bisphenols which are important in the preparation of epoxy resins and polyesters, are also known to be heat and oxygen sensitive and form degradation products which adversely affect the polymers subsequently made from them. Thus, bisphenol A is known to decompose with heat to form phenol and p-isopropylidene phenol. Additional heating can cause formation of complex non-volatile compounds. These degradation products, even in small concentrations, can cause a lowering of the molecular weight of polyesters. Color producing bodies can cause undesirable color in the bisphenol itself during its purification and in the epoxy resins and/or polyesters since both purification and manufacturing processes involve heating. The stabilization of polymers is believed to be achieved by incorporating a primary radical scavenger, usually a phenolic derivative. To combat the oxidation one must use also a hydroperoxide decomposer to be used together with the radical scavenger. Representative of hydroperoxide decomposers are thioesters and phosphites, such as dilaurylthiodipropionate and tri(nonylphenyl)phosphite. One reference in the J. Appld. Polym. Sci., Vol. 27, 951–955 (1982) reports the investigation of a diphosphonite* as both a hydroperoxide decomposer and a primary radical scavenger. The presence of metal ions is also thought to have an adverse affect on the color of bisphenols, probably by promoting degradation. Various other additives have been employed to inhibit the formation of the degradation products. Thus, alkaline earth phosphates, stannous oxide and oxalate, tin powder and tin dioxide, terephthalic and isophthalic acids, oxalic, sebacic and adipic acids and boron and antimony trioxides and their mixtures are taught as useful additives for providing thermal stability to bisphenols in British patent 890,432. Another patent, British 1,022,583, teaches that improved color stability is provided by the incorporation of oxalic, citric or tartaric acids or their alkali metal or ammonium salts during the bisphenol manufacturing process. The acids themselves or their ammonium salts are preferred and they may be added with the reactants or after the reaction is complete, but before the bisphenol is separated from the reaction mixture. U.S. Pat. No. 3,629,339 teaches the stabilization of phenols and bisphenols with an inorganic arsenic compound such as arsenic trioxide or ammonium and alkali metal arsenites. U.S. Pat. No. 4,160,110 teaches that various phthalic anhydrides are useful as distillation inhibitors against degradation of bisphenols. Thus, phthalic anhydride itself and tetrahydrophthalic anhydride are indicated as useful. Japanese patent 48097854 discloses stabilizing bisphenol A by distilling it in the presence of a polypropylene glycol, epoxy soybean oil, 2,2-bis-(p-glycidylphenyl)propane or a glycerol poly(oxypropylene) adduct. Bisphenols are stabilized against thermal decomposition by incorporating therein a quaternary aliphatic ester of ortho titanic acid according to the teachings of U.S. Pat. No. 4,359,590. A Japanese Kokoku Application No. 43-80421 teaches that the heat stability of bisphenol A can be improved by adjusting the pH to between 2.0 and 5.0 and adding a weak acid such as glycolic, thioglycolic and polyphosphoric acid. Among other acids tested in addition to the above for comparative purposes in the Japanese Patent Application were phosphorous, boric and lactic, none of which were considered to be effective. The lactic acid was no better than the uninhibited product with respect to color under conditions employed in the Japanese Patent Application.

*The inhibitor referred to is tetrakis(2,4-di-tert-butylphenyl)4,4'biphenylene diphosphonite, also known as P-EPQ.

SUMMARY OF THE INVENTION

The present invention is the discovery that certain hydroxy carboxylic acids, not hitherto employed as stabilizers, aact in a particularly beneficial manner. Lactic, malic and glyceric acids have been found to be superior to the hydroxy acids here-to-fore employed. These hydroxy carboxylic acids can be added to the feed reactants used to make the bisphenols or to the reaction mixture after the reaction is complete or at any point in between. The acids can also be employed as their ammonium or alkali metal salts. They are particularly useful in stabilizing the bisphenols during purification by distillation when exposed to elevated temperatures.

DETAILED DESCRIPTION OF THE INVENTION

Certain hydroxy carboxylic acids have been found to be excellent inhibitors against the degradation of bisphenols and especially for inhibiting the formation of degradation products which can cause color in the bisphenol itself or in the polymeric products made from it. The particular hydroxycarboxylic acids found to be useful are lactic, malic and glyceric, with lactic or malic being preferred.

The inhibitors employed by the art have been added to the feed reactants prior to the condensation reaction which forms the bisphenol. The art also teaches that the inhibitors or stabilizers can be added at any point thereafter so long as it is prior to the distillation which separates the bisphenol from the reaction mixture. The inhibitor hydroxy carboxylic acids of the present invention can also be added either to the reactants or in the reaction mixture, but preferably before the distillation of the bisphenol at which point degradation is most likely to occur. The inhibitors of the present invention perform well in either solution or in a melt containing the bisphenol.

The hydroxycarboxylic acids of this invention can be employed separately or in combination with each other or in combination with other known inhibitors or stabilizers. The operable amount of the inhibitor of the invention to be employed is in the range of from about 2 to about 300 ppm, based on the total weight of the bisphenol. A preferred amount is from about 5 to about 100 ppm and most preferred is an amount of from about 10 to about 30 ppm. Employing less than the operable range will not satisfactorily inhibit the degradation. While employing more than 300 ppm will probably not be deleterious, it is to no advantage.

TEST APPARATUS AND METHOD

A 4-neck, 2 L flask, containing a stirring device and thermometer, padded with nitrogen and fitted with a heating mantle was used to conduct the test for stabilizing bisphenols. Nitrogen pressure was maintained in the flask at 10 psig. A stainless steel mesh coupon was inserted through one of the necks and allowed to remain under the surface of the liquid mixture for one hour while the flask was heated to a temperature of 80° C. Stirring was continuous throughout the two-hour period of heating. A 20-gram sample of the mixture was removed at 1, 1½ and 2-hour intervals. The phenol and water was then stripped from the sample by a rotoevaporator at 180° C. The bisphenol was then checked for colour using a Klett colorimeter. The Klett readings were converted to APHA numbers based on ASTM (Pt-Co) P1209-69 standards.

The following experiments illustrate the inhibiting effect on the degradation of or the stabilization of the bisphenol by the compounds of the invention:

EXAMPLE 1

To a reaction mixture containing water, acetone, phenol and bisphenol A was added 20 ppm lactic acid. The mixture was then heated to a temperature of 180° C. and maintained thereat for two hours. The APHA color was measured prior to the addition of the lactic acid and from time to time during the two-hour period. The amount of the increase in color compared to that of the uninhibited bisphenol mixture is shown in Table I.

EXAMPLE 2

In the manner of Example 1, malic and glyceric acids were added to separate mixtures of the water, acetone, phenol and bisphenol A employed therein. The APHA color was measured prior to the addition of the acids and from time to time during a two-hour period after adding the acids of the invention while the temperature of the mixture was maintained at 180° C. The amount of the increase in color is shown in Table I along with a comparison of the uninhibited bisphenol mixture.

COMPARATIVE EXAMPLES

Various other compounds were tested as inhibitors for bisphenol under the same conditions employed in Example 1. Results of Examples 1 and 2 above along with a control and inhibitors known to the art are shown in Table I. The comparative inhibitors are designated A, B, C and D.

Other inhibitors known to the art and used commercially, including phosphoric acid, Phosphite 168# and P-EPQ, were tested in the same manner as that of Example 1. The inhibitors of the present invention were shown to be superior to these also.

This is tris(2,4-di-tert-butylphenyl)phosphite.

| Stabilizer Compound | APHA Color at | | | |
|---|---|---|---|---|
| | 0 hr. | 1 hr. | 1½ hrs. | 2.0 hrs. |
| None (control) | 24 | 41 | 49 | 59 |
| Lactic acid | same | 30 | 33 | 41 |
| Malic acid | same | 27 | 29 | 32 |
| Glyceric acid | same | 22 | 26 | 29 |
| (A) Citric acid | same | 33 | 38 | 45 |
| (B) Tartaric Acid | same | 41 | 49 | 55 |
| (C) Glycolic Acid | same | 54 | 63 | 80 |
| (D) Oxalic | same | 39 | 50 | 71 |

We claim:
1. In a process for inhibiting the degradation of a bisphenol in which a hydroxycarboxylic acid is employed as the inhibitor, the improvement which comprises employing as the inhibitor a compound selected from the group consisting of lactic, malic and glyceric acids and mixtures thereof.
2. The process of claim 1 wherein the inhibitor is in the form of its ammonium or alkali metal salt.
3. The process of claim 1 wherein the bisphenol is the derivative of a ketone and a phenolic compound.
4. The process of claim 3 wherein the bisphenol is bisphenol A.
5. The process of claim 1 wherein the amount of the inhibitor employed is in the range of from about 2 to about 300 ppm based on the weight of the bisphenol.
6. The process of claim 5 wherein the amount of the inhibitor employed as in the range of from about 5 to about 100 ppm.
7. The process of claim 5 wherein the amount of the inhibitor employed is in the range of from about 10 to about 30 ppm.
8. The process of claim 1 wherein the inhibition is accomplished during the purification of the bisphenol.
9. The process of claim 4 wherein the inhibitor is lactic acid.
10. The process of claim 4 wherein the inhibitor is malic acid.
11. The process of claim 4 wherein the inhibitor is glyceric acid.

* * * * *